United States Patent
Adel et al.

(10) Patent No.: US 9,151,712 B1
(45) Date of Patent: Oct. 6, 2015

(54) RULE CHECKING FOR METROLOGY AND INSPECTION

(75) Inventors: Michael Adel, Zirchon Yaakov (IL); Ellis Chang, Saratoga, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 862 days.

(21) Appl. No.: 12/130,685

(22) Filed: May 30, 2008

Related U.S. Application Data

(60) Provisional application No. 60/940,950, filed on May 30, 2007.

(51) Int. Cl.
*G01N 21/47* (2006.01)
*G01N 21/892* (2006.01)

(52) U.S. Cl.
CPC .............. *G01N 21/47* (2013.01); *G01N 21/892* (2013.01)

(58) Field of Classification Search
CPC ................ G01N 21/47; G01N 21/892; G01N 21/9501–21/9505; G01N 21/956; G01N 21/8851
USPC ............................................. 702/84, 155, 179
See application file for complete search history.

(56) References Cited

U.S. PATENT DOCUMENTS

| | | | | |
|---|---|---|---|---|
| 4,589,139 A * | 5/1986 | Hada et al. | .................... | 382/144 |
| 5,703,692 A * | 12/1997 | McNeil et al. | ................ | 356/445 |
| 6,609,086 B1 * | 8/2003 | Bao et al. | ....................... | 702/189 |
| 7,068,833 B1 * | 6/2006 | Ghinovker et al. | ........... | 382/144 |
| 2003/0229410 A1 * | 12/2003 | Smith et al. | .................... | 700/109 |
| 2005/0004774 A1 | 1/2005 | Volk et al. | | |
| 2007/0045575 A1 * | 3/2007 | Bruland | .................. | 250/559.13 |
| 2007/0096094 A1 * | 5/2007 | Levinski et al. | ................ | 257/48 |
| 2008/0176045 A1 * | 7/2008 | Zhang et al. | ............... | 428/195.1 |
| 2008/0237586 A1 * | 10/2008 | Sun et al. | ........................ | 257/48 |

* cited by examiner

*Primary Examiner* — Mischita Henson
(74) *Attorney, Agent, or Firm* — Joshua D. Isenberg; JDI Patent

(57) ABSTRACT

A design feature in a design file including a pattern to be formed on a substrate may be selected as a metrology target, alignment target or inspection proxy. Metrology or inspection may be performed on the substrate using a printed feature on the substrate that corresponds to the design feature as a metrology target or inspection proxy.

38 Claims, 4 Drawing Sheets

RULE CHECKING FOR METROLOGY AND INSPECTION

CLAIM OF PRIORITY

This application claims the benefit of priority of commonly-assigned U.S. Provisional Patent Application No. 60/940,950, filed May 30, 2007, the entire contents of which are incorporated herein by reference.

FIELD OF THE INVENTION

This invention generally relates to substrate processing and more particularly to metrology and inspection of substrates in semiconductor fabrication.

BACKGROUND OF THE INVENTION

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

During each semiconductor fabrication process, defects such as particulate contamination and pattern defects may be introduced into semiconductor devices. Such defects may be found either randomly on a specimen surface or may be repeated within each device formed on a specimen. For example, random defects may be caused by events such as an unexpected increase in particulate contamination in a manufacturing environment and an unexpected increase in contamination in process chemicals that may be used in fabrication of a semiconductor device. A number of tools have been developed to inspect wafers for such defects.

In addition, as integrated circuit device geometries continue to shrink, it has become more important to perform metrology following each fabrication step, e.g., to verify that design features are properly printed or that features in successive layers are properly aligned with respect to each other. Manufacturers often use optical techniques to perform non-destructive inspection and analysis of semiconductor wafers. Such techniques often require a feature to be purpose-built on the wafer for use as a standard for calibration of tools performing inspection or metrology.

Prior inspection and metrology methods place targets for metrology or proxies for inspection in the scribe lines between adjacent die or at predetermined test sites in the die. Targets or proxies placed in scribe lines may be less accurate in predicting actual chip performance and yield than targets in the die. Methods have been proposed to automatically generate recipes for CD-SEM metrology where a set of specific metrology locations are input into the recipe in advance. However, placing metrology targets or inspection proxies in the die is a technically difficult procedure due to process compatibility and space restrictions.

It is within this context that embodiments of the present invention arise.

BRIEF DESCRIPTION OF THE DRAWINGS

Other objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

According to embodiments of the present invention, instead of designing and printing metrology and alignment targets or inspection proxies in a scribe line or on a die, features from a design file may be used as metrology and alignment targets or inspection proxies. Embodiments of the invention provide methods and apparatus that enable metrology and inspection of substrates, such as semiconductor wafers and reticles, without having to insert dedicated proxies. This may be achieved by searching the design file to identify inspection or metrology sites that meet specific criteria and providing a ranked list of locations to a recipe generator. In an alternative embodiment of the invention, alignment targets, useful for enabling exposure tool alignment for lithographic patterning by either optical e-beam or other means may be identified by methods described herein. In this case the recipe modification may be that of the lithographic system. In a similar fashion, these alignment marks may serve the metrology or inspection tool's internal alignment system and their locations may be used to modify the metrology or inspection recipe.

Figure 1:
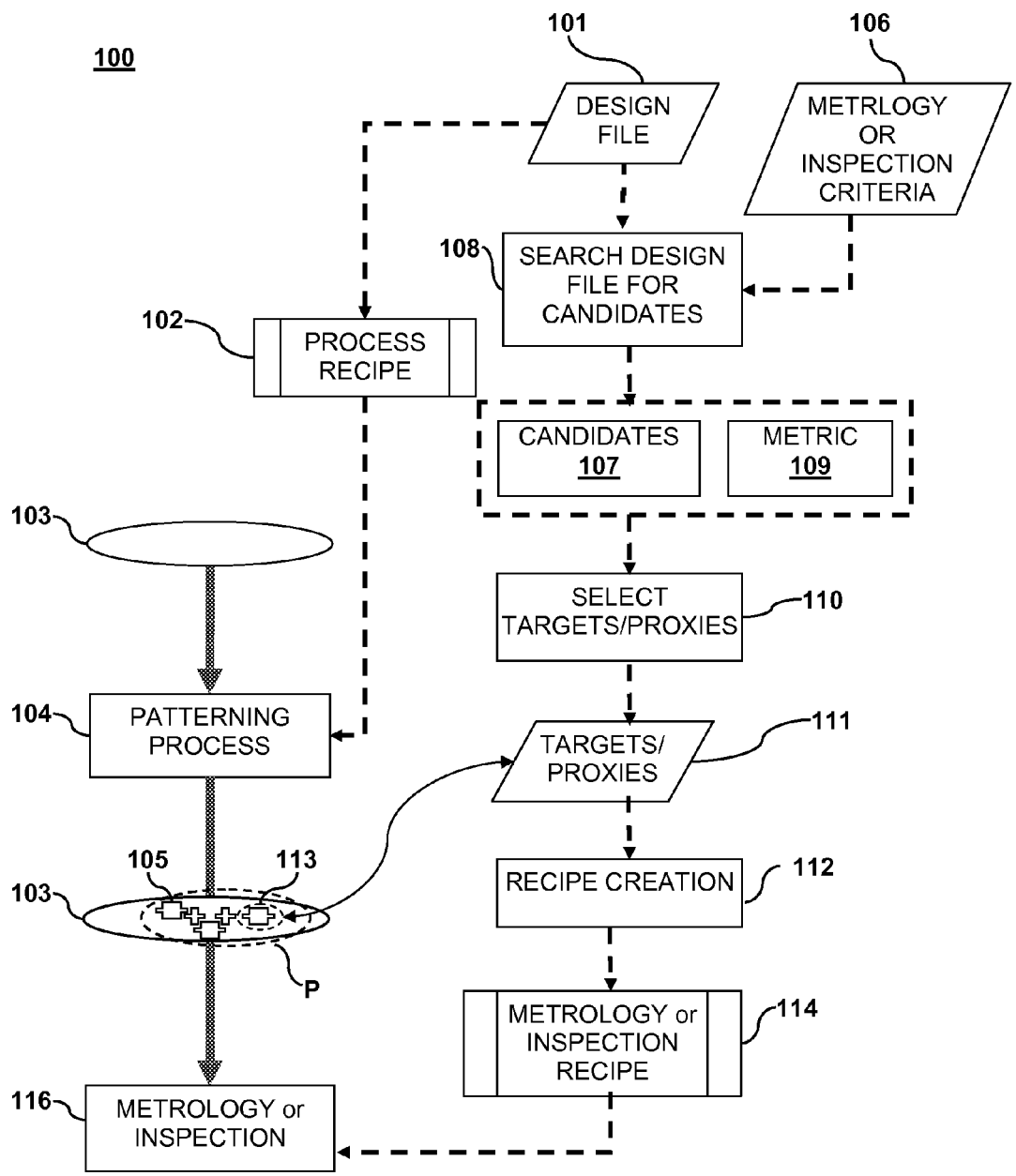
FIG. 1 is a flow diagram illustrating a version of a method according to an embodiment of the present invention.

By way of example, FIG. 1 illustrates a version of a computer implemented method 100 according to an embodiment of the present invention. A design file 101 is used to generate a process recipe 102 that may be used for a patterning process 104. The patterning process may involve one or more lithography steps that form a pattern P on a substrate 103. The pattern P includes features 105, which may correspond to structures in an integrated circuit. By way of example, the substrate 103 may be a semiconductor wafer on which the integrated circuit is formed. Alternatively, the substrate 103 may be a reticle having a lithography pattern used to form the integrated circuit on a semiconductor wafer. The design file 101 contains information relating to the pattern to be formed on the substrate 103. Such information may be in a binary format, such as a graphic data system (GDS) format. Specifically, the design file 101 may include a binary format representation of planar geometric shapes corresponding to the features 105, as well as text labels and other information in hierarchical form.

According to the method 100, a design feature may be selected from the design file 101 as a metrology target or inspection proxy. Metrology or inspection may be performed on the substrate 103 using a printed feature 113 on the substrate 103 that corresponds to the design feature as a metrology target or inspection proxy.

By way of example, a program may define criteria 106 that need to be met to allow a pre-existing feature or set of features in a single layer or in multiple layers in the design file 101 to function as metrology targets or inspection proxies when printed on a wafer. The criteria 106 may include, among other things, geometric and spatial criteria for a feature or set of features in the pattern to be formed on the substrate 103. Using these criteria, the design file 101 may be searched at 108 for suitable candidate features 107. Such a search may be performed e.g. in a fashion similar to searches performed by existing electronic design automation (EDA) tools, such as design rule check applications.

Figure 2A:
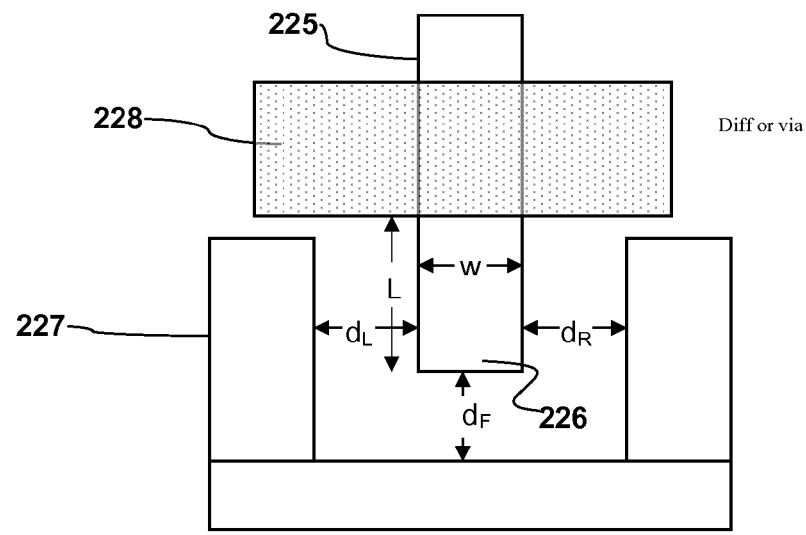
FIG. 2A is a schematic plan view of a feature in a design file that may be used as an inspection proxy according to an embodiment of the present invention.

By way of example, a user may define a pattern of interest (POI) such as "line-end-pull-back", e.g., as shown in FIG. 2A. In such a case, a candidate feature 225 may be characterized by a more or less linear structure with a termination 226 surrounded on three sides by a neighboring structure 227. The candidate feature 225 and neighboring structure 227 may be formed in the same layer and may be made of the same material, e.g., polysilicon or metal. An overlying structure 228 of a different material, e.g., a via-filling material or diffusion barrier, may overlap a portion of the candidate feature 225. Relevant criteria for such a POI include a width w of the candidate feature, distances $d_L$, $d_R$ and $d_F$ between the candidate feature and left, right and front sides of the neighboring structure 227 and a length L of the candidate feature from the termination 226 to the overlying structure 228. Commonly available design rule checking software may identify all occurrences of this specific POI on one or multiple GDS layers. An example of such software is known as Design-based Binning (DBB), which is available from KLA-Tencor Corporation of San Jose, Calif. The software may also output design attributes such as pattern density, minimum line space, minimum line width, etc. These design attributes may be used for ranking of candidates.

Figure 2B:
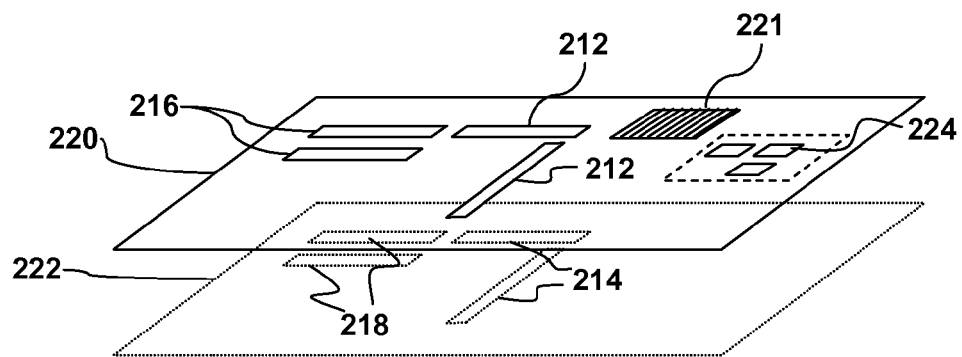
FIG. 2B is a schematic diagram of a version of a pattern to be formed on a substrate illustrating examples of features that can be used as metrology targets or inspection proxies in embodiments of the present invention.

The results of the search may include a matching metric 109 that measures correlation of the candidates 107 with the predetermined criteria 106. FIG. 2B shows alternative examples of features in the design file 101 that may be identified as candidates 107 for inspection proxies and/or metrology targets. By way of example, and without limitation, in the case of overlay metrology, the criteria 106 may involve the existence of orthogonal features 212, 214 overlapping one another on subsequent layers 220, 222. Such features may be used for "box-in-box" overlay measurements. Alternatively, the criteria 106 may involve the existence of or parallel features 216, 218 overlapping one another on subsequent layers 220, 222. Such features may be used as periodic overlay metrology targets or alignment targets. Preferably, the orthogonal features 212, 214 and/or parallel features 216, 218 are large enough to be resolved by the metrology system but small enough to fit easily in the metrology system's field of view. For overlay or critical dimension or film thickness metrology by optical means, the criteria may include a specific range of spatial frequencies, i.e. pitch or characteristic dimensions.

The candidates 107 may include features 221 characterized by a pitch p (repeated spacing between adjacent parallel lines) that a metrology or inspection tool can resolve. In some cases, the features may actually be selected to ensure that the contrary is true, i.e. that the feature is unresolved. This may be important for metrology purposes to ensure that only a specific diffraction order is collected by the metrology sensor, e.g. the zero order. This may prove beneficial due to considerations of systematic error reduction and accuracy of modeling. In another embodiment, the spatial frequency criterion is selected such that only the first order of diffraction is collected by the metrology sensor, which proves beneficial in signal processing and systematic error reduction. In addition, the design criteria may be chosen such that the search 110 identifies features that will fit within a field of view of the metrology tool. Identification of such features is particularly useful for inspection and/or metrology using a CD-SEM. Furthermore, the candidates 107 may include one or more features 224 characterized by a particular size, shape and material composition suitable for use as an inspection proxy. For example, features having dimensions, shapes and material composition similar to particulate contaminants may be selected as inspection proxies. Such features may be used to verify that an inspection tool can detect particles of similar size, shape and material composition as the features 224.

Figure 2C:
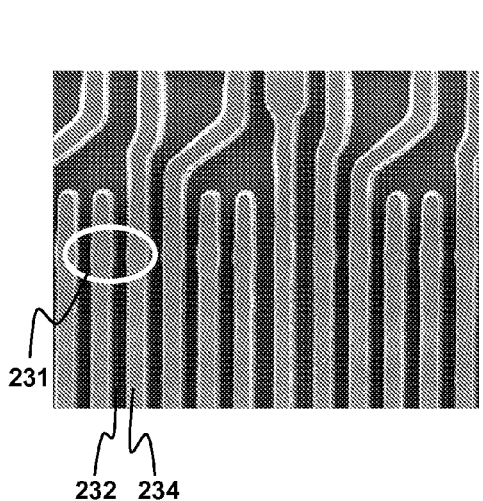
FIG. 2C is a micrograph of a lithographically formed structure that may be selected as an inspection proxy according to an embodiment of the present invention.
Figure 2D:
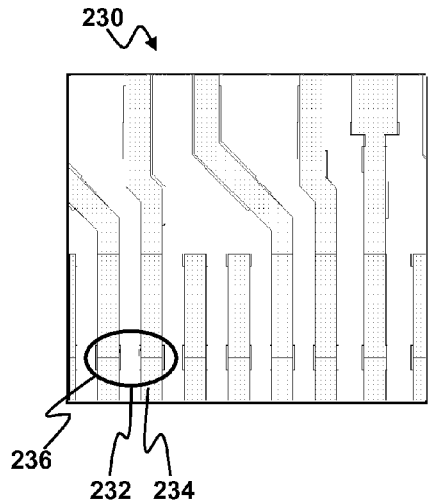
FIG. 2D illustrates a portion of a structure in a design file corresponding to a lithographically formed structure of the type shown in FIG. 2C.

Alternatively, inspection proxies may include portions of a design that are subject to bridging defects in one or more layers containing metal features. For example, the micrograph of FIG. 2C illustrates bridging metal defects in the form of undesired and unintended formation of metal 231 bridging gaps 232 between adjacent linear features 234. A corresponding portion of a GDS layout 230 defining the gaps 232 and linear features 234 is shown in FIG. 2D. Such features, particularly at locations 236 where bridging metal is likely to form, e.g., due to the smallness of the gap and/or other criteria, may be selected as candidates 107 for inspection proxies.

Referring again to FIG. 1, the results (e.g., the candidates 107) may be ranked according to predetermined sort criteria such as the matching metric 109, followed by location on the substrate 103. The ranked output 111 may then be uploaded into an automated recipe creation application 112, which may generate a metrology and/or inspection recipe 114. The ranked output 111 may include metrology targets and/or inspection proxies that correspond to features 113 on the substrate 103. The metrology/inspection recipe 114 may select from among the ranked output particular features 113 to use in an inspection and/or metrology process 116 performed on the substrate. It is noted that the results 111 may include multiple potential targets. The metrology or inspection recipe may select a subset of the ranked candidates 107 that allow sufficient field level sampling to enable an appropriate model of the spatial dependence of the overlay to be determined. The results of the search 110 may also include the location of each candidate feature 107 and a graphic data system (GDS) "cut out" of the feature. It is worthy to point out that the alignment, metrology or inspection feature may be identified within the operational device features in the design, but it may also reside in the areas known as dummy-fill areas which are added for the purpose of controlling pattern density in otherwise unused real estate.

Figure 3:
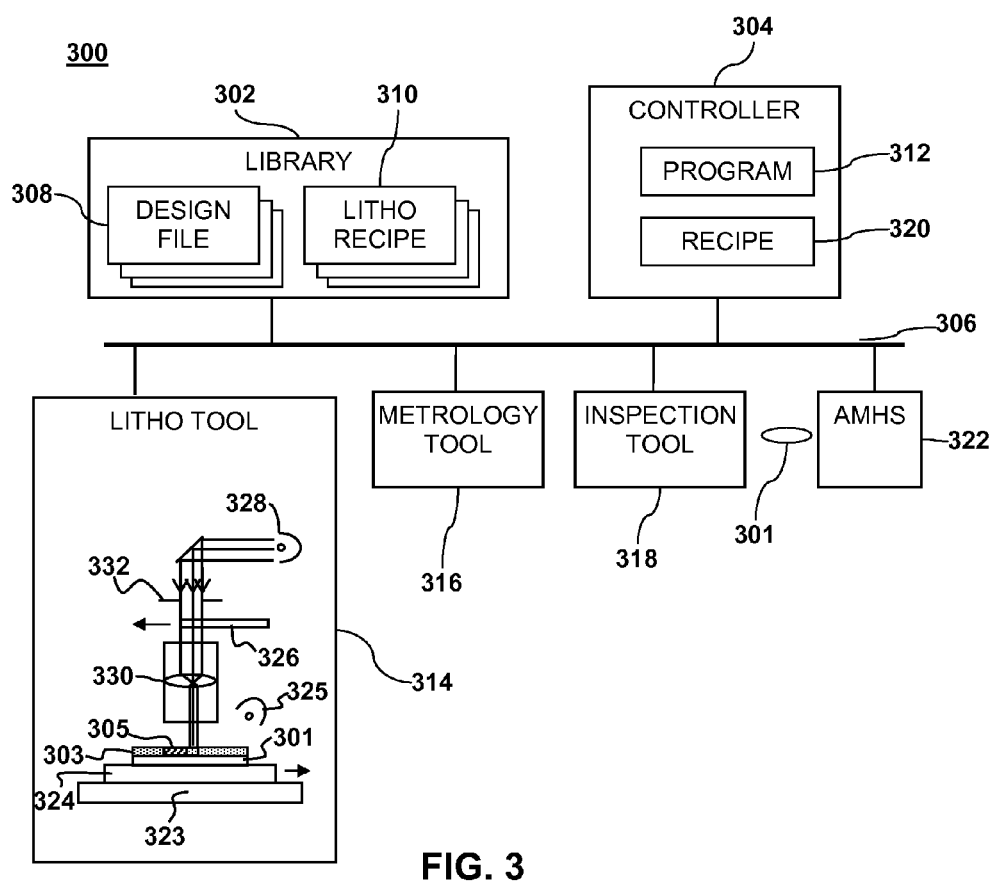
FIG. 3 is a block diagram of a version of a semiconductor fabrication system configured to implement an inspection/metrology method according to an embodiment of the present invention.

FIG. 3 illustrates an example of a semiconductor fabrication system 300 configured to implement an inspection/metrology method of the type described above. Specifically, the system 300 includes a data library 302 and a controller 304 which may be operable connected over a data bus 306. The data library 304 may be include design files 308 and lithography recipes 310 stored in a data storage device, such as a computer memory or mass storage device. It is noted that the design files 308 and lithography recipes 310 may be stored on separate storage devices. The system 300 may further include a lithography tool 314, a metrology tool 316 and/or an inspection tool 318 which may exchange data and/or commands over the data bus 306. The lithography tool 314, metrology tool 316 and/or inspection tool 318 may operate in accordance with a recipe 320 which may be implemented by suitably configured software running on the controller 304. Substrates 301 may be transferred from one of these tools to another by an automated material handling system (AMHS) 322 such as a robot or overhead track system.

The controller 304 may be programmed with a program 312 that implements certain aspects of the method 100 described above. The controller 304 may be a general purpose computer that acts as a specific purpose computer when running programs such as the program 312. Specifically, the program 312 may include instructions that, when executed, select a design feature in one or more of the design files 308 for a pattern to be formed on a substrate 301 as a metrology target or inspection proxy. The program 312 may include further instructions that cause the metrology tool 316 to perform metrology or cause the inspection tool to perform an inspection on the substrate 301 using a printed feature on the substrate 301 that corresponds to the design feature as a metrology target. Alternatively, the may include instructions that cause the inspection tool 318 to perform an inspection of the substrate 301 using a printed feature on the substrate 301 that corresponds to the design feature as an inspection proxy.

By way of example, the lithographic patterning tool 314 may include a scanner or stepper developer. Such developers are similar in operation to a slide projector or a photographic enlarger. Such tools are often used in photolithographic processes used to form microscopic circuit elements on the surface of a semiconductor wafer. In the patterning tool 314, a substrate 301 may be retained on a stage 324, which may include a chuck, e.g., a vacuum chuck or an electrostatic chuck. Elements of a circuit or other component to be created on the IC are reproduced in a pattern of transparent and opaque areas on the surface of a photomask or reticle 326. The pattern on the reticle 326 often corresponds to a pattern for a single die or chip for an integrated circuit. The pattern on the reticle may be generated based on one or more of the design files 308. Light from a source 328 passes through the reticle 326 and forms an image of the reticle pattern. The image is focused and reduced by a lens 330, and projected onto the surface of the substrate 301 that is coated with a photoresist 303. The focused image on the resist 303 is often referred to as an exposure field 305. After exposure, the coated substrate 301 may be chemically developed, causing the photoresist 303 to dissolve in certain areas according to the amount of light the areas received during exposure.

This transfers the pattern on the reticle 326 to the resist 303. The patterning tool 314 may be equipped with heater elements 325, such as heat lamps, to facilitate heating of the resist 303 either before or after exposure, e.g., to harden it.

The patterning tool 314 may be a stepper with an alignment system 323 that moves the substrate 301 after exposing one die so that another portion of the substrate 301 may be exposed with the same exposure field 303. The patterning tool 314 may also be configured as a scanner. Scanners are steppers that increase the length of the exposure field 303 by moving the reticle 326 and stage 324 in opposite directions to each other during the exposure. Instead of exposing the entire field at once, the exposure is made through an "exposure slit" 332 that is as wide as the exposure field 305, but only a fraction of its length (e.g., a 9×25 mm slit for a 35×25 mm field). The image from the exposure slit 332 is scanned across the exposure area on the substrate 301.

Examples of suitable metrology tools 316 include overlay tools, spectroscopic ellipsometers, electrical monitoring tools, stylus-based surface profilers, resistivity metrology tools, focus/exposure line monitors, thin film analyzers and scanning electron microscopes, in particular a critical dimension scanning electron microscope (CD-SEM). Examples overlay tools include Archer series tools, e.g., Archer 100, Archer AIM+, or Archer XT+ from KLA-Tencor Corporation of San Jose, Calif. and their equivalents. Examples of spectroscopic ellipsometers include Spectra Fx 200 optical thin film metrology systems from KLA-Tencor Corporation of San Jose, Calif. and equivalents. Examples of electrical monitoring tools include Quantox XP in-line, real-time electrical monitoring and characterization tools from KLA-Tencor Corporation and their equivalents. Examples of stylus-based surface profilers include HRP 240/340 Series Alpha-Step IQ, and P-16 profilers from KLA-Tencor and their equivalents. Examples of resistivity metrology tools include RS-100 resistivity measurement tools from KLA-Tencor and their equivalents. Examples of focus/exposure line monitors include MPX Focus/Exposure Line Monitors from KLA-Tencor and their equivalents. Examples of thin film analyzers include ASET-5X, Spectra FX 100, and MetriX 100 systems from KLA-Tencor. Examples of scanning electron microscopes include eV300 defect review tools from KLA-Tencor and equivalents.

Examples of suitable inspection tools 318 include, but are not limited to, high-resolution imaging inspection systems, backside inspection modules, patterned wafer inspection tools, broadband bright field inspection tools, macro defect inspection tools, optical surface analyzers, edge inspection tools, reticle inspection systems and the like. Examples of imaging inspection systems include series 2360 high-resolution imaging inspection systems from KLA-Tencor of San Jose, Calif. and equivalents. Examples of broadband bright-field inspection tools include 2800 series Broadband Bright field DUV/UV/visible inspection systems from KLA-Tencor of San Jose, Calif. and equivalents. Examples of backside inspection modules include SP1 series backside inspection modules from KLA-Tencor of San Jose, Calif. and equivalents. Examples of macro defect inspection tools include Viper 2430 systems from KLA-Tencor of San Jose, Calif. and equivalents. Examples of optical surface analyzers include Candela CS1 optical surface analyzers from KLA-Tencor of San Jose, Calif. and equivalents. Examples of edge inspection tools include VisEdge CV300 edge inspection systems from KLA-Tencor of San Jose, Calif. and equivalents. Examples of reticle inspection systems include TeraScan and TeraStar series systems from KLA-Tencor of San Jose, Calif. and equivalents.

It is noted that processing of a substrate 301 with the lithography tool 314 may determine the inspection or metrology process that follows. Consequently, the Choice of lithography recipe 310 may determine the specific types of metrology targets and/or inspection proxies that the program 312 searches for in the design file 308. For example, a lithography recipe 310 may call for the lithography tool 314 to form a pattern in a layer of material that overlies another pattern in an underlying layer. The pattern may be formed using one or more of the design files 308. In such a case, it may be desirable to determine the degree of alignment between the two patterns, e.g., using an overlay tool. In such a case, the program 312 may search the design files 308 for candidate. In such a case, it may be desirable to perform overlay metrology with the metrology tool 316. As a result the program 312 may search the relevant design files 308 for candidate features meeting the criteria for an overlay target.

Figure 4:
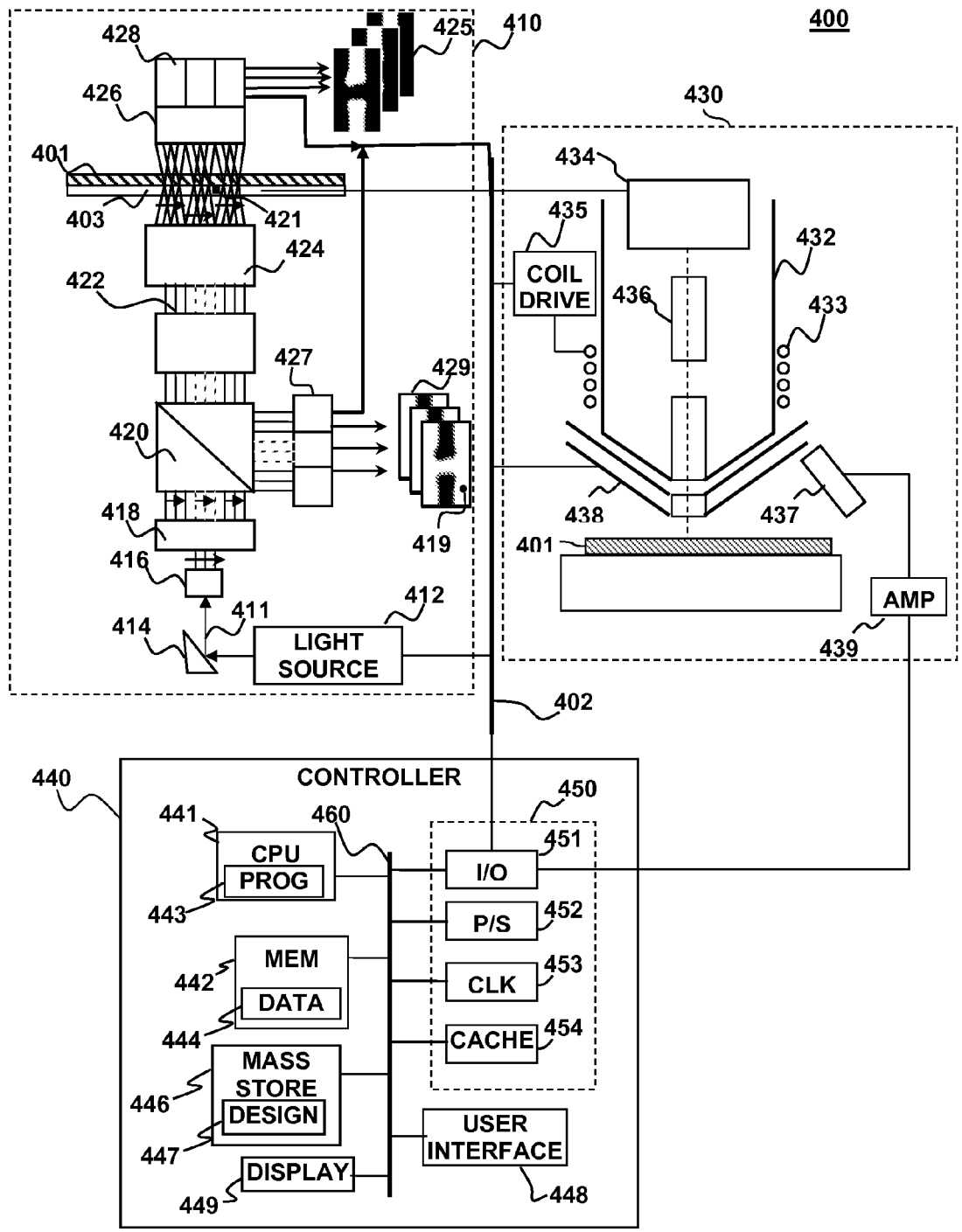
FIG. 4 is a block diagram of a version of a metrology/inspection apparatus according to an embodiment of the present invention.

FIG. 4 illustrates a metrology/inspection apparatus 400 according to an embodiment of the present invention. The apparatus 400 includes may include an inspection tool 410 and/or a metrology tool 430 and a controller 440. The inspection tool 410, metrology tool 430 and controller 440 may communicate with each other through a data bus 402. The controller 440 may include a central processor unit (CPU) 441 and a memory 442 (e.g., RAM, DRAM, ROM, and the like). The CPU 441 may execute a program 443, portions of which may be stored in the memory 442. The memory 442 may include data 444 used by or generated by the program 443. The controller 440 may optionally include a mass storage device 446 such as a disk drive, CD-ROM drive, tape drive, or the like to store programs and/or data. The controller 440 may also include well-known support circuits 450, such as input/output (I/O) circuits 451, power supplies (P/S) 452, a clock (CLK) 453 and cache 454. The controller 440 may also optionally include a user interface unit 448 and display unit 449 to facilitate interaction between the controller 440 and a user. The display unit 449 may be in the form of a cathode ray tube (CRT) or flat panel screen that displays text, numerals, or graphical symbols. The user interface 448 may include a keyboard, mouse, joystick, light pen or other device. The preceding components may exchange signals with each other via an internal bus 460. The controller 440 may be a general purpose computer that becomes a special purpose computer when running code that implements embodiments of the present invention as described herein. It is noted that the inspection tool 410 and metrology tool 430 may each have separate controllers associated with them. Alternatively, both tools may operate using a single controller. A single controller is shown in the example depicted in FIG. 4 for the sake of simplicity.

The inspection tool may be any of the tools listed above with respect to inspection tool 316. By way of example, and without limitation, the inspection tool 410 may be an optical substrate inspection tool. A commercially-available example of an optical substrate inspection tool is a TeraScan™ DUV Reticle Inspection System, commercially available from KLA-Tencor Corporation of San Jose, Calif. In such an inspection tool 410, one or more light sources 412 may provide incident light 411. As used herein, the term "light" generally refers to electromagnetic radiation in a range of frequencies running from infrared through the ultraviolet, roughly corresponding to a range of vacuum wavelengths from about 1 nanometer ($10^{-9}$ meters) to about 100 microns. The light 411 may be characterized by one or more wavelengths within the electromagnetic spectrum (including but not limited to ultraviolet, visible, infrared and the like). By way of example and without limitation, the light source 412 may include one or more lasers that provide the incident light 411 in the form of one or more laser beams. Alternatively, the light source 412 may be a highly focused broadband source, such as lamp, that can provide adequate energy photons.

A beam steering mechanism 414 and other optical components may steer the incident light 411 such that the incident light 411 is normally incident on a substrate 401 such as a wafer, mask or reticle, through an optional pellicle 403 covering the test surface of the substrate 401.

The substrate 401 may be mounted to a stage that allows for indexing and scanning of the substrate.

Additional optical components may be disposed between the beam steering mechanism 414 and the substrate 401. For example an acoustic scanner 416 may separate the incident light into multiple beams. A beam replicator 418 may replicate each of these beams in different wavelength ranges. The replicated beams may pass through an optical circulator 420 and one or more pixel filters 422. The pixel filter 422 is an optical subsystem that creates various pixel sizes. Smaller pixels are used to achieve sensitivity for smaller defects. In some systems, multiple filters may be mounted to a turret for quick replacement. Alternatively, different pixel sizes may be obtained through use of a zoom lens system. After passing through the pixel filters 422, the replicated beams are focused by an imaging objective 424 onto a surface of the substrate 401. Collection optics 426 mounted opposite the objective 424 may collect light transmitted by the substrate 401 and couple the transmitted light to photosensors 428 which may be coupled to the controller 430, e.g., via I/O circuits 451. Signals from the photosensors 428 can be used to generate images 425 of the substrate 401 from the detected transmitted light. Light reflected by the substrate may be collimated by the imaging objective 424 and deflected by the optical circulator 420 to another set of photosensors 427, which may be coupled to the controller 430, e.g., via I/O circuits 451. Signals from the photosensors 427 can be used to generate images 429 of the substrate 401 from the detected transmitted light. A defect 421 on the test surface of the substrate 401 may be detected by comparing the images 425 and 429. For example, a feature 419 appearing in reflected light image 429 but not in the transmitted light image 425 may be marked as contamination defect 421.

By way of example, and without limitation of embodiments of the invention, the metrology tool 430 may include an overlay tool, a thin film tool, such as a spectroscopic ellipsometer, an electron beam tool such as a critical dimension scanning electron microscope (CD-SEM), or other tool listed above with respect to metrology tool 316. By way of example, and without loss of generality, the metrology tool 430 may be a thin film metrology tool. Alternatively, as shown in FIG. 4, the metrology tool 430 may include an electron beam tool, such as a scanning electron microscope. It is noted that a scanning electron microscope be used as either a metrology tool or inspection tool. By way of example, the electron microscope may be an eDR5200 defect review system from KLA-Tencor Corporation of San Jose, Calif. Such a system may generally include an electron beam column 432 with an electron source 434, beam optics 436 an immersion lens 438. The electron beam source 434, beam optics 436 and immersion lens 438 may be controlled by signals generated by the controller 440 and transmitted via the I/O circuits 451 in response to the program 443 and/or user inputs.

Electrons from the electron beam column 432 are focused onto a surface of a substrate 401, which may be an integrated circuit wafer. The electrons may be scanned across the surface of the substrate 401 by magnet deflecting fields provided by one or more scanning coils 433. Current is provided to the coils 433 via a scanner driver 435. The scanner driver may operate in response to signals from the controller 440. Electrons striking the target 401 are either backscattered or initiate secondary emission. A detector 437 may collect such backscattered or secondary electrons and generate a signal proportional to the amount of backscattering or secondary emission. The signal may be amplified by an amplifier 439. The amplified signal may be coupled to the controller 440 e.g., via the I/O circuits and used to generate one or more images of the surface of the substrate 401.

By way of example, the program 443 may be configured to implement the method 100. Specifically, the program 443 may include instructions that, when executed, implement a method of the type described above. Specifically, the instructions may, when executed select a design feature in one or more of the design files 447 for a pattern to be formed on a substrate 401 as a metrology target or inspection proxy. The design file 447 may be stored in the mass storage 446. It is noted that the mass storage may be part of the controller or may be a separate device coupled to the mass storage over a network. The program 443 may include further instructions that cause the metrology tool 430 to perform metrology or cause the inspection tool to perform an inspection on the substrate 401 using a printed feature on the substrate 401 that corresponds to the design feature as a metrology target. Alternatively, the may include instructions that cause the inspection tool 410 to perform an inspection of the substrate 401 using a printed feature on the substrate 401 that corresponds to the design feature as an inspection proxy. The data 444 in memory 442 may include the results of a search of a design file for candidates for metrology targets and/or inspection proxies. By way of example, candidates by be stored in memory 442 in the form of GDS cutouts corresponding to one or more metrology targets or inspection proxies on a substrate 401. Alternatively, the data 444 may include one or more criteria for choosing such targets from among the features in the design file.

Embodiments of the present invention avoid the need to insert metrology or inspection structures in a die. This has a number of advantages of existing solutions. For example, scribe line space that might otherwise be allocated for metrology targets and/or inspection proxies is made available for other purposes such as electrical test structures, and alignment structures. Furthermore, the width of the scribeline may be further reduced and hence the amount of space available for manufacturing increased. In addition, metrology targets and/or inspection proxies need not be inserted in a die where they may have detrimental effects on device performance due to process interactions. The time consuming and iterative activity associated with metrology and inspection target design and insertion may also be avoided. Furthermore, metrology and inspection recipes may be automatically generated based entirely on design data.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A computer-implemented method, comprising:
analyzing a computer-readable design file using a computer, wherein the design file defines a pattern to be formed on a substrate, the pattern including circuit features that correspond to operational device features in an integrated circuit, to select a circuit feature in the pattern as a metrology target for performing a metrology that requires a dedicated metrology target for performing the metrology, wherein the selected circuit feature is not a dedicated metrology target; and
performing the metrology on the substrate with a computer-controlled metrology tool using a printed feature on the substrate that corresponds to the selected circuit feature as the metrology target, wherein the circuit feature is selected by performing a search of the design file for one or more circuit feature candidates from said circuit features that meet one or more pre-determined geometric and/or spatial criteria before the metrology tool performs the metrology, wherein the one or more circuit feature candidates are characterized by a pitch that is too small to be resolved by the metrology tool to ensure that only a specific diffraction order of light scattered from the printed feature is collected by the metrology tool during said performing the metrology.

2. The method of claim 1, further comprising forming the pattern on the substrate.

3. The method of claim 1 wherein the substrate is a semiconductor wafer.

4. The method of claim 1, wherein the substrate is a reticle.

5. The method of claim 1 wherein the selected circuit feature includes two or more parallel lines.

6. The method of claim 1 wherein the selected circuit feature includes two or more perpendicular lines.

7. The method of claim 1 wherein the selected circuit feature is a location susceptible to bridging metal contacts.

8. The method of claim 1 wherein the selected circuit feature is characterized by a user-defined pattern of interest.

9. The method of the claim 8 wherein the user-defined pattern of interest is a line-end-pull-back pattern.

10. The method of claim 1 wherein the selected circuit feature is within an operational device feature in a design defined by the design file.

11. The method of claim 1 wherein the selected circuit feature is within a dummy-fill area of a design defined by the design file.

12. The method of claim 1 wherein the selected circuit feature is chosen to fit within a field of view of the metrology tool used to perform the metrology.

13. The method of claim 12 wherein the metrology or inspection is performed using a critical dimension scanning electron microscope (CD-SEM).

14. The method of claim 1 wherein the metrology is performed using a tool selected from the group consisting of overlay tools, and critical dimension (CD) metrology tools.

15. The method of claim 1 wherein the predetermined geometric and/or spatial criteria include a specific range of spatial frequencies.

16. The method of claim 15, further comprising generating a matching metric for one or more of the circuit feature candidates, wherein the matching metric is based on a correlation of a candidate with the predetermined geometric and/or spatial criteria.

17. The method of claim 16, further comprising ranking the one or more circuit feature candidates according to correlation with the predetermined geometric and/or spatial criteria.

18. The method of claim 16 wherein performing metrology includes uploading one or more of the circuit feature candidates into an automated recipe creation application and generating a metrology recipe.

19. The method of claim 1, wherein the selected circuit feature is selected as an overlay metrology target and wherein performing metrology on the substrate with the computer-controlled metrology tool using the printed feature on the substrate that corresponds to the selected circuit feature includes performing overlay metrology using the selected feature as an overlay metrology target.

20. The method of claim 1, wherein the selected circuit feature is selected as a critical dimension (CD) metrology target and wherein performing metrology on the substrate with the computer-controlled metrology tool using the printed feature on the substrate that corresponds to the selected circuit feature includes performing CD metrology using the selected feature as a CD metrology target.

21. The method of claim 1, wherein the specific diffraction order is zero order.

22. The method of claim 1, wherein the specific diffraction order is first order.

23. A metrology apparatus, comprising:
a metrology tool;
a controller operably coupled to the metrology tool, the controller having a memory and a processor configured to implement instructions that, when executed cause the controller to analyze a design file, wherein the design file defines a pattern to be formed on a substrate, the pattern including circuit features that correspond to operational device features in an integrated circuit, to select a circuit feature in the pattern as a metrology target for performing a metrology that requires a dedicated metrology target for performing the metrology, wherein the selected circuit feature is not a dedicated metrology target; and cause the controller to direct the metrology tool to perform metrology on the substrate using a printed feature on the substrate that corresponds to the selected circuit feature as the metrology target, wherein the circuit feature is selected by performing a search of the design file for one or more circuit feature candidates from said circuit features that meet one or more pre-determined geometric and/or spatial criteria before the metrology tool performs the metrology, wherein the one or more circuit feature candidates are characterized by a pitch that is too small to be resolved by the metrology tool to ensure that only a specific diffraction order of light scattered from the printed feature is collected by the metrology tool during said performing the metrology.

24. The apparatus of claim 23 wherein the design file is stored in the memory.

25. The apparatus of claim 23 wherein the design file is stored in storage internal or external to the controller.

26. The apparatus of claim 23 wherein the selected circuit feature includes two or more parallel lines.

27. The apparatus of claim 23 wherein the selected circuit feature includes two or more perpendicular lines.

28. The apparatus of claim 23 wherein the selected circuit feature is a location susceptible to bridging metal contacts.

29. The apparatus of claim 23 wherein the selected circuit feature is characterized by a user-defined pattern of interest.

30. The apparatus of claim 29 wherein the user-defined pattern of interest is a line-end-pull-back pattern.

31. The apparatus of claim 23 wherein the selected circuit feature is within an operational device features in a design defined by the design file.

32. The apparatus of claim 23 wherein the selected circuit feature is within a dummy-fill area of a design defined by the design file.

33. The apparatus of claim 23 wherein the selected circuit feature is chosen to fit within a field of view of a metrology tool used to perform the metrology.

34. The apparatus of claim 33 wherein the metrology is performed using a critical dimension scanning electron microscope (CD-SEM).

35. The apparatus of claim 23 wherein the metrology tool is selected from the group consisting of overlay tools and critical dimension (CD) metrology tools.

36. The apparatus of claim 23, wherein the specific diffraction order is zero order.

37. The apparatus of claim 23, wherein the specific diffraction order is first order.

38. A non-transitory computer-readable storage medium having embodied therein computer-readable instructions for implementing a metrology method on an apparatus having a controller coupled to a metrology tool, the metrology method comprising:
analyzing a design file, wherein the design file defines a pattern to be formed on a substrate, the pattern including circuit features that correspond to operational device features in an integrated circuit, to select a circuit feature in the pattern as a metrology target for performing a metrology that requires a dedicated target for performing the metrology, wherein the selected circuit feature is not a dedicated metrology target; and
performing the metrology on the substrate with the metrology tool using a printed feature on the substrate that corresponds to the selected circuit feature as the metrology target, wherein the selected circuit feature is selected by performing a search of the design file for one or more circuit feature candidates from said circuit features that meet one or more pre-determined geometric and/or spatial criteria before the metrology or inspection tool performs the metrology, wherein the one or more circuit feature candidates are characterized by a pitch that is too small to be resolved by the metrology tool to ensure that only a specific diffraction order of light scattered from the printed feature is collected by the metrology tool during said performing the metrology.

* * * * *